(12) United States Patent
Frush et al.

(10) Patent No.: US 6,382,575 B1
(45) Date of Patent: May 7, 2002

(54) INSTRUMENT HOLDER FOR USE IN CONJUNCTION WITH A MOUNTING PLATE

(75) Inventors: Donald R. Frush; Thomas J. Bussell, both of Warsaw, IN (US)

(73) Assignee: Paragon Medical, Inc., Pierceton, IN (US)

( * ) Notice: Subject to any disclaimer, the term of this patent is extended or adjusted under 35 U.S.C. 154(b) by 0 days.

(21) Appl. No.: 09/627,812

(22) Filed: Jul. 28, 2000

(51) Int. Cl.⁷ ................................................ A47B 96/06
(52) U.S. Cl. ............... 248/220.31; 248/505; 211/85.13; 422/297; 422/300
(58) Field of Search ............................... 248/231.9, 505, 248/220.22, 71, 220.31; 422/297, 300; 206/443, 370; 211/120, 89.01, 124, 85.13, 69.8

(56) References Cited

U.S. PATENT DOCUMENTS

| | | | |
|---|---|---|---|
| 2,926,790 A | * | 3/1960 | Dieck |
| 4,135,868 A | * | 1/1979 | Schainholz |
| 5,211,915 A | | 5/1993 | Monch |
| 5,213,776 A | * | 5/1993 | Maniero et al. |
| 5,215,726 A | | 6/1993 | Kudla |
| 5,258,166 A | | 11/1993 | Janzer |
| 5,284,632 A | | 2/1994 | Kudla |
| 5,294,413 A | | 3/1994 | Riihimaki |
| 5,305,876 A | | 4/1994 | Brigham |
| 5,307,933 A | | 5/1994 | Guignet |
| 5,346,075 A | | 9/1994 | Nichels |
| 5,411,136 A | | 5/1995 | Brigham |
| 5,422,067 A | | 6/1995 | Barney |
| 5,424,048 A | | 6/1995 | Riley |
| 5,433,929 A | | 7/1995 | Riihimaki |
| 5,433,930 A | | 7/1995 | Taschner |
| 5,449,069 A | | 9/1995 | Pijanowski |
| 5,490,975 A | | 2/1996 | Dane |
| 5,492,671 A | | 2/1996 | Kraft |
| 5,505,916 A | | 4/1996 | Berry |
| 5,518,115 A | | 5/1996 | Latulippe |
| 5,525,314 A | | 6/1996 | Hurson |
| 5,531,702 A | * | 7/1996 | Baker et al. |
| 5,542,533 A | | 8/1996 | Vargas |
| 5,599,512 A | | 2/1997 | Latulippe |
| 5,681,539 A | | 10/1997 | Riley |
| 5,690,223 A | | 11/1997 | Wood |
| 5,759,502 A | | 6/1998 | Spencer |
| 5,762,202 A | | 6/1998 | Atad |
| 5,827,487 A | | 10/1998 | Homes |
| 6,012,577 A | | 1/2000 | Lewis |

* cited by examiner

*Primary Examiner*—Ramon O. Ramirez
*Assistant Examiner*—Korie H. Chan
(74) *Attorney, Agent, or Firm*—James D. Hall; Ken C. Decker

(57) ABSTRACT

An instrument bracket, primarily for holding medical instrumentation, having a clip part which is mountable to a plate and a holder part. The plate may form a part of a sterilization tray or similar container. The clip part is of an inverted U-shaped configuration having spaced upwardly projecting legs. The clip part fits about the holder part which is flexible and shape retaining and which includes a recess to accommodate the instrumentation. The clip part compresses and retains the holder part and is secured to the plate.

8 Claims, 5 Drawing Sheets

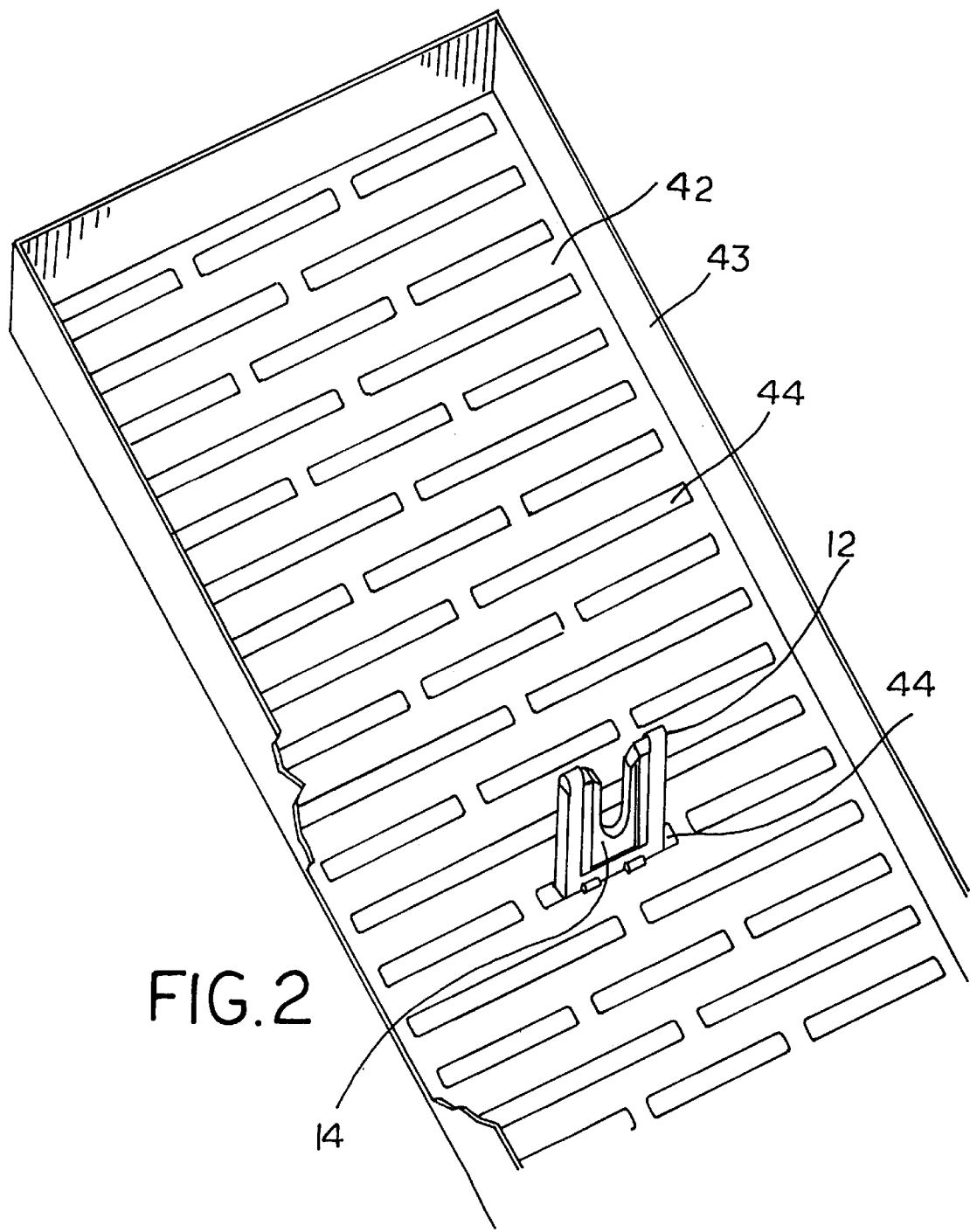

INSTRUMENT HOLDER FOR USE IN CONJUNCTION WITH A MOUNTING PLATE

SUMMARY OF THE INVENTION

This invention relates to a holder for instrumentation with specific application to a medical instrument bracket used in conjunction with a tray or similar container.

The instrument bracket of this invention includes a clip part which is of flexible yet semi-rigid form and a holder part which is of resilient, shape retaining form. The clip part includes upwardly projecting spaced apart legs and is of an inverted U-shaped configuration. The clip part fits into the holder part and is compressed between the legs of the clip part when the clip part is mounted to the instrument plate or container. The holder part includes a recess for receiving the instrumentation.

Heretofore, instrumentation brackets have been formed of such material as silicone which provides flexibility but sometimes does not provide enough rigidity for more heavy instrumentation, thus allowing the instruments to migrate or move during normal handling of the container. Metal brackets are expensive and sometimes prone to failure due to either bending or the loosening of fasteners. Additionally, some metal brackets are cumbersome to utilize and do not provide a firm grip of the instrument within the container. There have been brackets formed of the combination of a metal frame with a silicone insert. These brackets use rivets, screws or other hardware for attachment to the top or upper surface instrument plate or base. Such combination brackets do not easily permit separation of the insert from the metal frame for cleaning or replacement, nor are they easily detached from the instrument plate for replacement or relocation.

In this invention, a two-piece bracket is provided allowing for easy assembly and mounting of the bracket as well as thorough sterilization and cleaning. The silicone insert or holder part can be replaced simply and expediently when necessary.

Accordingly, it is an object of this invention to provide a bracket for medical instrumentation which is of reliable and economical construction.

Still another object of this invention is to provide an instrument bracket which is for medical instrumentation and which is of two-part separable construction.

Still another object of this invention is to provide an instrument bracket which is for medical instrumentation and which includes component parts which partially encloses the instruments for retention within the holder.

Still another object of this invention is the ability to easily revise, replace, relocate and remove the brackets.

Still another object of this invention is for the clip and holder to be attached to the instrument plate or container without the use of assembly tools or fasteners/hardware.

Other objects of this invention will become apparent upon a reading of the following description.

BRIEF DESCRIPTION OF THE DRAWINGS

A preferred embodiment of this invention has been chosen for purposes and discussion wherein:

FIG. 2 is a fragmentary perspective of a tray showing the bracket of FIG. 1 mounted to the tray.

DESCRIPTION OF THE PREFERRED EMBODIMENT

Figure 1:
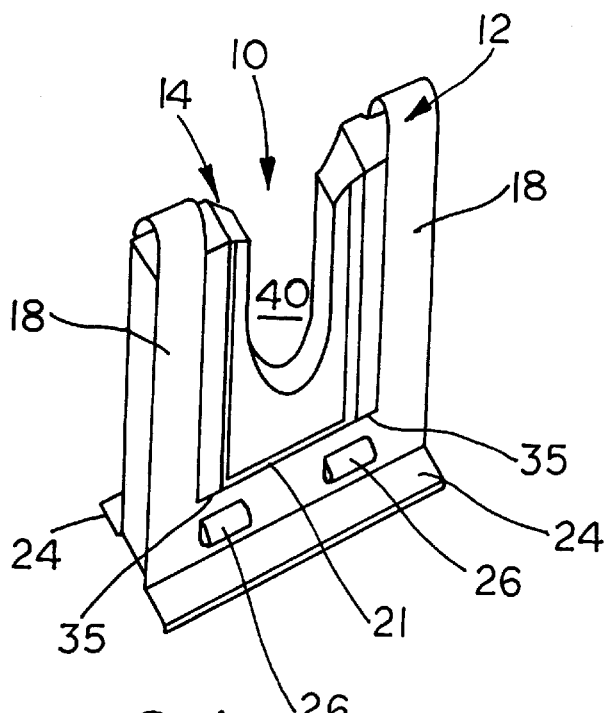
FIG. 1 is a perspective view of the bracket of this invention.
Figure 3:
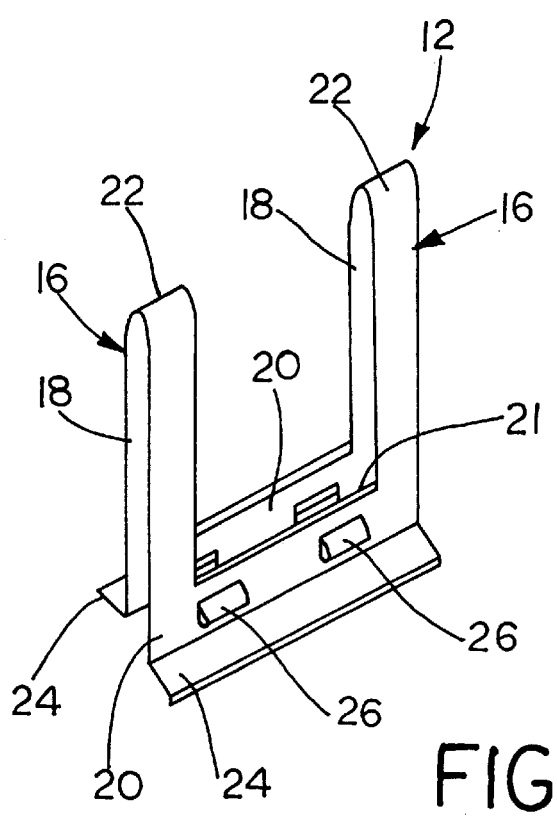
FIG. 3 is a perspective view of the clip part of the bracket.
Figure 4:
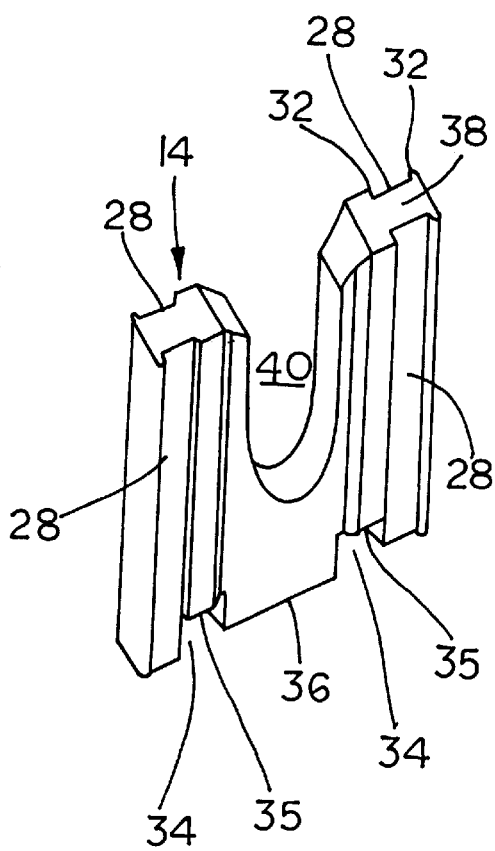
FIG. 4 is a perspective view of one form of the holder part for the bracket.
Figure 5:
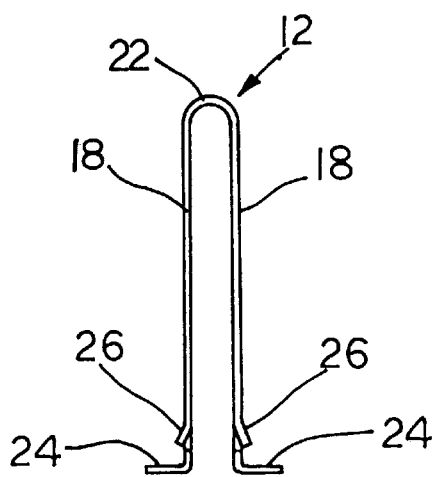
FIG. 5 is a elevational end view of the clip part of the bracket.
Figure 6:
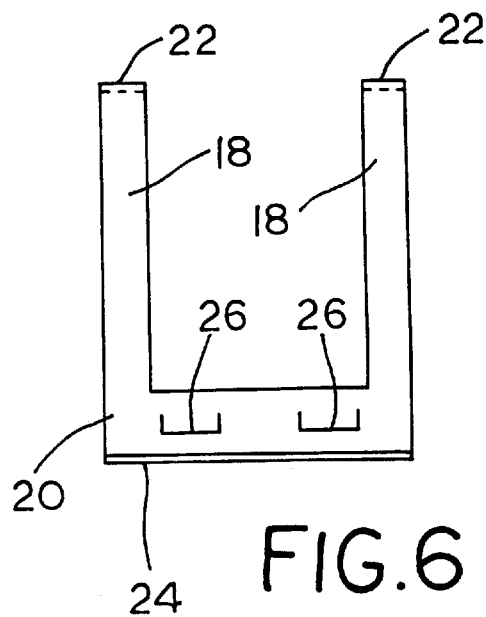
FIG. 6 is a front elevational view of the clip part.
Figure 7:
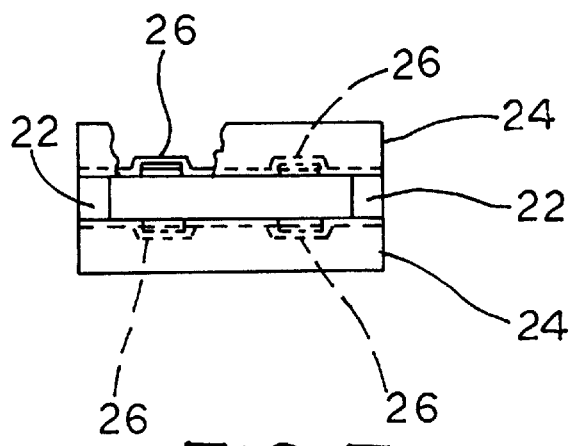
FIG. 7 is a bottom view of the holder part with a portion broken away for illustrative purposes.
Figure 8:
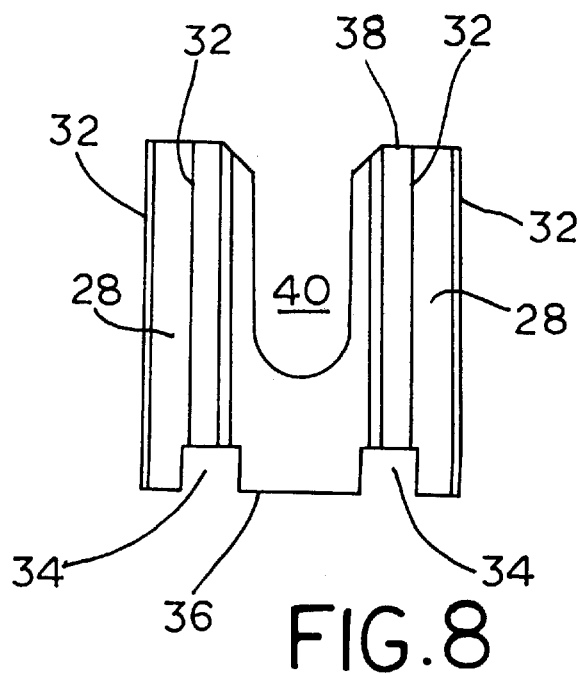
FIG. 8 is a side elevational view of one form of the holder part as seen in FIG. 4.
Figure 9:
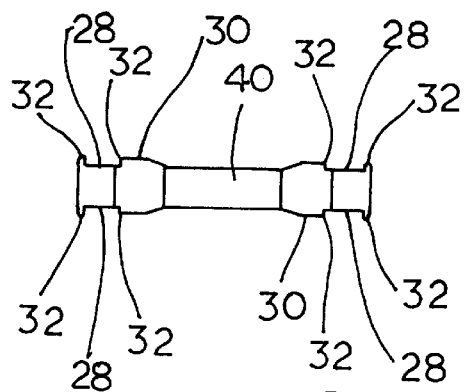
FIG. 9 is a bottom view of the holder part of FIG. 8.
Figure 10:
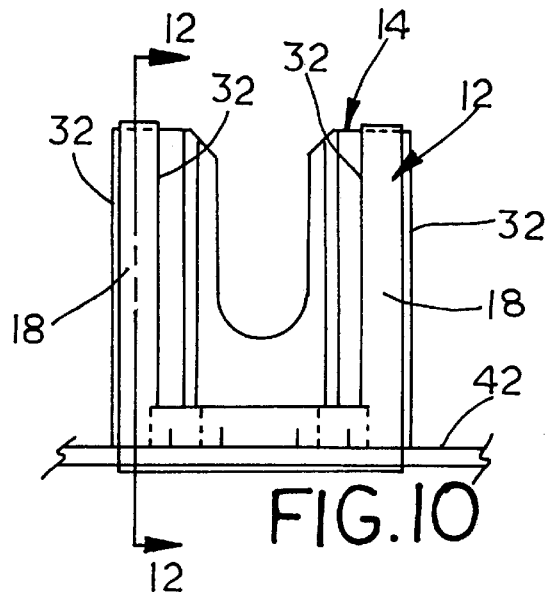
FIG. 10 is an elevational view of the bracket of FIG. 1 shown attached to a mounting plate.
Figure 11:
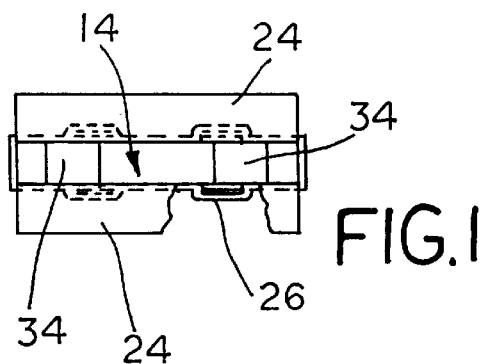
FIG. 11 is a bottom view of the bracket of FIG. 1 with portions broken away for purposes of illustration.

Bracket 10 of this invention includes a clip part 12 and holder part 14. Clip part 12 is of a semi-rigid, yet flexible form being constructed from a plastic or metal, such as a stainless steel. Holder part 14 is formed of a flexible shape retaining material such as medical grade silicone. Clip part 12 is an inverted U-shaped configuration having opposed sides 16 each formed of upwardly extending spaced legs 18 which extend upwardly from a base 20. The legs 18 of one side 16 are connected to the legs 18 of the other side 16 by inter-connecting webs 22. Each side 16 at its base 20 includes an outwardly extending foot 24 and upwardly located, outwardly directed barbs or tangs 26.

Figure 14:
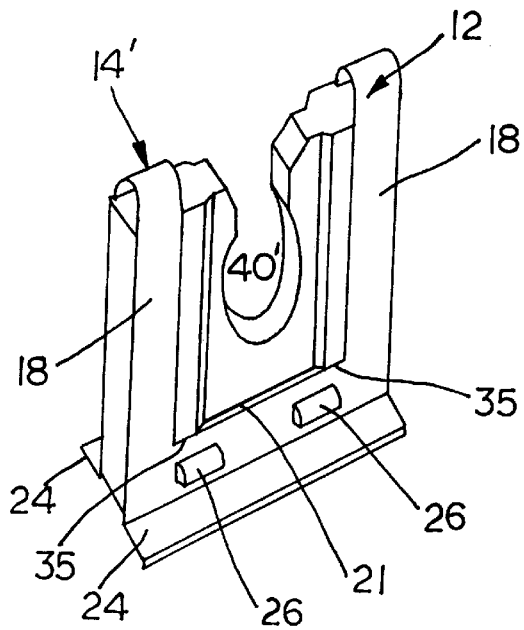
FIG. 14 is a perspective view of the bracket showing the holder part in modified form.
Figure 15:
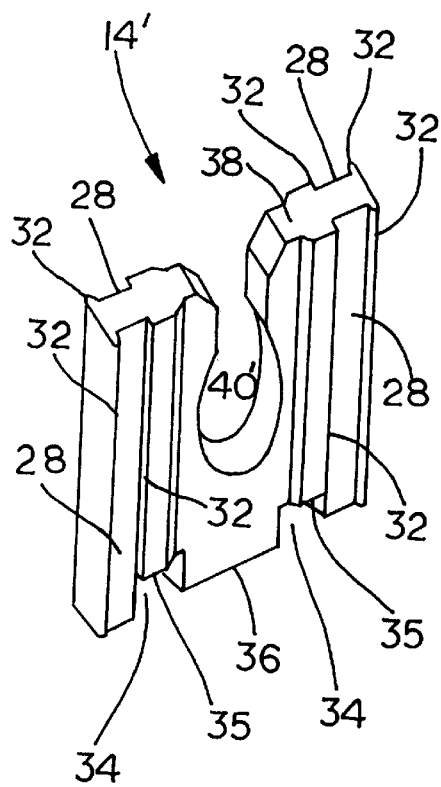
FIG. 15 a perspective view of the holder part of FIG. 14.
Figure 16:
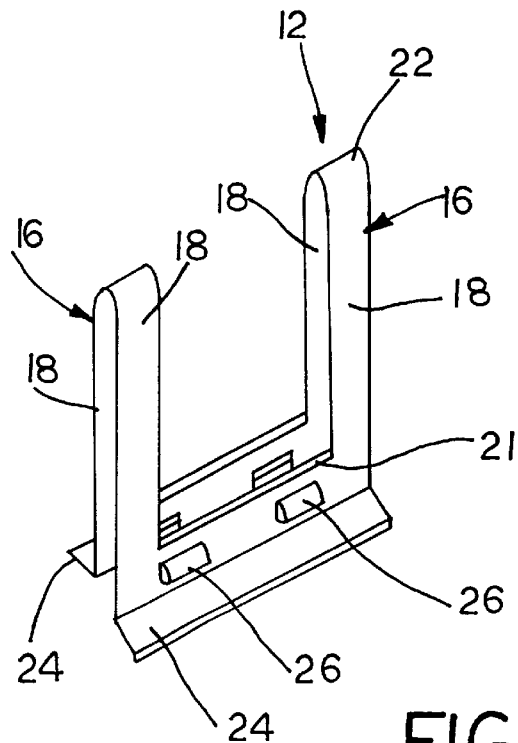
FIG. 16 is another perspective view of the clip part like FIG. 3.

Holder part 14 includes oppositely located vertically extending channels 28 which extend on each of the sides 30 of the part and which are located between opposed ribs 32. A pair of spaced notches 34 are formed in the lower edge 36 of the clip part. The upper edge 38 of holder part 14 is interrupted by a centrally located recess 40 which may assume various configurations for the receipt of the instrumentation, such as recess 40' shown in the modified holder part 14' of FIGS. 14 and 15. Holder part 14' is the same as part 14 except for the shape of recess 40'. Recess 40, 40' is preferably located centrally between channels 28.

Figure 12:
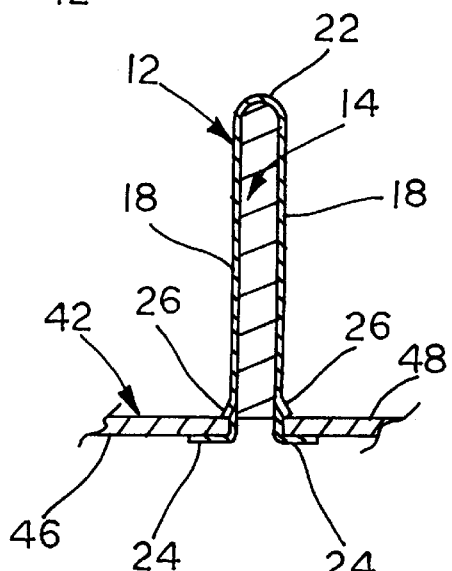
FIG. 12 is a sectional view taken along line 12—12 of FIG. 10.
Figure 13:
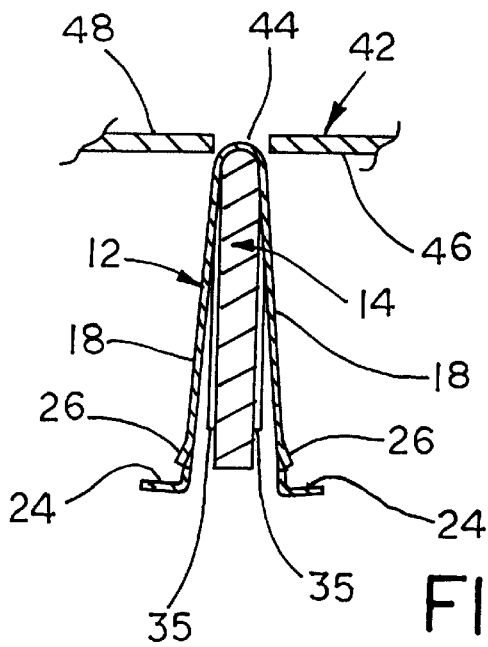
FIG. 13 is a sectional view of the bracket of FIG. 1 in preparation for mounting to the plate.

To use bracket 10, holder part 14, 14' is fitted between sides 16 of clip part 12 with legs 18 of the sides fitting into channels 28 in the holder part. A suitable plate 42 with slots 44 is provided to accommodate bracket 10 and the instrumentation. Plate 42 may form a part of the lower wall of a tray 43, such as a sterilization tray or it may be a separate wall part which removably fitted into a container such as a tray. To attach bracket 10, feet 24 of the clip part are squeezed towards each other causing compression of the inserted holder part 14, 14'. The clip part and compressed holder part are then inserted upwardly as a unit through slot 44 in plate 42 until legs 24 abut the bottom surface 46 of the plate and barbs 26 overly the upper surface 48 of the plate. At that time, feet 24 are released allowing slight extension of the flexible clip part, to cause the clip part to be compressed and wedge fitted in slot 44 of plate 42 and restrained against either upward or downward movement relative to the plate by barbs 26 and feet 24 which are positioned in an interference fit on each side of the plate as illustrated in FIG. 12. When necessary to either clean, replace or move holder part 14, 14', bracket 10 may be easily removed by compressing legs 18 causing further compression of holder part 14 and a slight reduction in thickness of the bracket sufficient to allow barbs 26 to clear slot 44 and allow the bracket to be pushed downwardly through the slot and out of attachment with plate 42.

Notches 34 in holder part 14, 14' each provide for a shoulder 35 which protrudes from adjacent rib 32 and which overlaps and rests upon upper edge 21 of base 20 as best seen in FIG. 1 to secure the holder part against downward movement relative to the clip part. Holder part 14 is restrained against lateral movement relative to clip part 12 by the inter-fit of legs 18 into channels 28 of the holder part.

Recess 40' in holder 14' allows for a free fit of the instrumentations so as to allow for full sterilization about the instrument. The upper most periphery of recess 40' is necked inwardly, thus providing a reduced slot which retards vertical movement of the instrument relative to the bracket yet allowing at the base of the recess sufficient space about the instrument to provide full sterilization.

It is to be understood that the invention is not to be limited to the details above given but may be modified within the scope of the appended claims.

What is claimed:

1. An instrument bracket comprising a clip part and a holder part used in combination with a plate, said plate having a slot therein, said clip part having first and second sides each including a base and spaced upwardly projecting legs terminating in upper ends, one of said legs of said first side joined by a web to one of said legs of said second side, the other of said legs of said first side joined by another web to the other of said legs of said second side, said holder part having a instrument receiving recess and being removably located between said first and second sides of the clip part, said clip part fitted into said plate slot with said sides thereof compressing said holder part to retain the holder part within the clip part, said holder part recess located between said legs of each said first and second sides.

2. The bracket of claim 1 wherein said clip part interlocks with said plate at said slot.

3. The bracket of claim 2 wherein said clip part is semi-rigid having limited flexibility, said holder being resilient and shaped retaining.

4. The bracket of claim 3 wherein said clip part is formed of metal, and said holder part is formed of silicone.

5. The bracket of claim 3 wherein said clip part is formed of plastic, and said holder is formed of silicone.

6. The bracket of claim 1 wherein said clip part includes oppositely extending feet and oppositely extending barbs spaced upwardly relative to the clip part from said legs, said clip part and holder part extending upwardly through said plate slot, said plate having a lower surface and an upper surface, said clip part feet engaging said lower surface of said plate and said barbs engaging said upper surface of said plate to secure said clip part and holder part to the plate.

7. The bracket of claim 6 wherein said holder part includes spaced channels, said legs of said clip part seated in said channels.

8. The bracket of claim 7 wherein said holder part includes a shoulder, said shoulder seated upon said base of said clip part.

* * * * *